United States Patent
Ruman et al.

(10) Patent No.: US 9,339,424 B2
(45) Date of Patent: May 17, 2016

(54) ABSORBENT ARTICLE HAVING AN ABSORBENT ASSEMBLY WITH INTEGRAL CONTAINMENT FLAPS

(71) Applicant: Kimberly-Clark Worldwide, Inc., Neenah, WI (US)

(72) Inventors: Marcille Faye Ruman, Oshkosh, WI (US); Kathleen Irene Bennett, Neenah, WI (US); Aster E. Kammrath, Neenah, WI (US); Andrew Neubauer, Neenah, WI (US); Joseph J. Sina, Appleton, WI (US); Joseph Daniel Coenen, Kaukauna, WI (US); Lori Roocks, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 100 days.

(21) Appl. No.: 14/062,278

(22) Filed: Oct. 24, 2013

(65) Prior Publication Data

US 2015/0119844 A1    Apr. 30, 2015

(51) Int. Cl.
*A61F 13/494* (2006.01)
*A61F 13/56* (2006.01)
*A61F 13/49* (2006.01)

(52) U.S. Cl.
CPC .......... *A61F 13/5633* (2013.01); *A61F 13/4906* (2013.01); *A61F 13/49406* (2013.01); *A61F 13/49413* (2013.01); *A61F 13/49453* (2013.01); *A61F 2013/49493* (2013.01); *A61F 2013/5666* (2013.01)

(58) Field of Classification Search
CPC .......... A61F 13/4752; A61F 13/49413; A61F 13/49446; A61F 13/49453; A61F 2013/4948; A61F 2013/49493
USPC .......................... 604/385.25–385.28, 385.14
See application file for complete search history.

(56) References Cited

U.S. PATENT DOCUMENTS

| | | |
|---|---|---|
| 1,397,579 A | 11/1921 | Guinzburg |
| 4,100,324 A | 7/1978 | Anderson et al. |
| 4,205,679 A | 6/1980 | Repke et al. |
| 4,573,986 A | 3/1986 | Minetola et al. |
| 4,597,760 A | 7/1986 | Buell |
| 4,610,681 A | 9/1986 | Strohbeen et al. |
| 4,663,220 A | 5/1987 | Wisneski et al. |
| 4,699,621 A | 10/1987 | Stevens et al. |
| 4,701,172 A | 10/1987 | Stevens |
| 4,747,846 A | 5/1988 | Boland et al. |

(Continued)

FOREIGN PATENT DOCUMENTS

| | | |
|---|---|---|
| EP | 0459178 | 12/1991 |
| EP | 0217032 | 2/1992 |

(Continued)

OTHER PUBLICATIONS

Written Opinion and International Search Report of International Application No. PCT/IB2014/065275; Feb. 5, 2015; 12 pages.

*Primary Examiner* — Lynne Anderson
(74) *Attorney, Agent, or Firm* — Armstrong Teasdale LLP

(57) ABSTRACT

An absorbent assembly includes a liquid permeable bodyside liner, a liquid impermeable backsheet, and an absorbent structure disposed between the liner and the backsheet. A pair of laterally opposed containment flaps is integrally formed from the bodyside liner.

25 Claims, 9 Drawing Sheets

(56) References Cited

U.S. PATENT DOCUMENTS

| | | | |
|---|---|---|---|
| 4,846,825 A | 7/1989 | Enloe et al. | |
| 4,940,464 A | 7/1990 | Van Gompel et al. | |
| 5,046,272 A | 9/1991 | Vogt et al. | |
| 5,064,421 A | 11/1991 | Tracy | |
| 5,104,116 A | 4/1992 | Pohjola | |
| 5,114,420 A | 5/1992 | Igaue et al. | |
| 5,224,405 A | 7/1993 | Pohjola | |
| 5,226,992 A | 7/1993 | Morman | |
| 5,236,430 A | 8/1993 | Bridges | |
| 5,284,703 A | 2/1994 | Everhart et al. | |
| 5,350,624 A | 9/1994 | Georger et al. | |
| 5,385,775 A | 1/1995 | Wright | |
| 5,476,458 A | 12/1995 | Glaug et al. | |
| 5,482,765 A | 1/1996 | Bradley et al. | |
| 5,486,166 A | 1/1996 | Bishop et al. | |
| 5,490,846 A | 2/1996 | Ellis et al. | |
| 5,492,751 A | 2/1996 | Butt, Sr. et al. | |
| 5,496,429 A | 3/1996 | Hasse et al. | |
| 5,593,401 A | 1/1997 | Sosalla et al. | |
| 5,601,544 A | 2/1997 | Glaug et al. | |
| 5,607,416 A | 3/1997 | Yamamoto et al. | |
| 5,624,420 A | 4/1997 | Bridges et al. | |
| 5,624,424 A | 4/1997 | Saisaka et al. | |
| 5,662,638 A | 9/1997 | Johnson et al. | |
| 5,674,215 A * | 10/1997 | Ronnberg | 604/385.28 |
| 5,704,928 A * | 1/1998 | Morita et al. | 604/385.23 |
| 5,706,524 A | 1/1998 | Herrin et al. | |
| 5,714,156 A | 2/1998 | Schmidt et al. | |
| 5,766,389 A | 6/1998 | Brandon et al. | |
| 5,772,825 A | 6/1998 | Schmitz | |
| 5,779,831 A | 7/1998 | Schmitz | |
| 5,820,973 A | 10/1998 | Dodge, II et al. | |
| 5,870,778 A | 2/1999 | Tharpe | |
| 5,885,266 A | 3/1999 | Chihani et al. | |
| 6,057,024 A | 5/2000 | Mleziva et al. | |
| 6,113,717 A | 9/2000 | Vogt et al. | |
| 6,369,291 B1 | 4/2002 | Uchimoto et al. | |
| 6,380,292 B1 | 4/2002 | Gibes et al. | |
| 6,383,170 B1 | 5/2002 | Mishima et al. | |
| 6,394,991 B1 | 5/2002 | Takei et al. | |
| 6,552,245 B1 | 4/2003 | Roessler | |
| 6,562,017 B1 | 5/2003 | Nakaoka et al. | |
| 6,576,809 B1 | 6/2003 | Inoue et al. | |
| 6,585,840 B2 | 7/2003 | Rabe et al. | |
| 6,605,071 B1 | 8/2003 | Gray et al. | |
| 6,605,173 B2 | 8/2003 | Glaug et al. | |
| 6,645,190 B1 | 11/2003 | Olson et al. | |
| 6,716,205 B2 * | 4/2004 | Popp et al. | 604/385.24 |
| 6,753,455 B2 | 6/2004 | Chmielewski | |
| 6,822,136 B1 | 11/2004 | Niemeyer et al. | |
| 6,899,780 B2 | 5/2005 | Rajala et al. | |
| 6,916,750 B2 | 7/2005 | Thomas et al. | |
| 6,939,335 B2 | 9/2005 | Franke et al. | |
| 6,962,578 B1 | 11/2005 | Lavon et al. | |
| 6,969,378 B1 | 11/2005 | Vukos et al. | |
| 6,969,441 B2 | 11/2005 | Welch et al. | |
| 7,014,632 B2 | 3/2006 | Takino et al. | |
| 7,047,572 B2 | 5/2006 | Hopkins | |
| 7,227,051 B2 | 6/2007 | Mitsui et al. | |
| 7,264,686 B2 | 9/2007 | Thorson et al. | |
| 7,666,175 B2 | 2/2010 | Trennepohl | |
| 7,727,217 B2 | 6/2010 | Hancock-Cooke | |
| 7,777,094 B2 | 8/2010 | Mori et al. | |
| 7,794,441 B2 | 9/2010 | Ashton et al. | |
| 7,803,244 B2 | 9/2010 | Siqueira et al. | |
| 7,854,022 B2 | 12/2010 | Warren et al. | |
| 7,901,390 B1 | 3/2011 | Ashton et al. | |
| 8,109,916 B2 | 2/2012 | Wennerback | |
| 8,168,028 B2 | 5/2012 | Schneider et al. | |
| 8,212,102 B2 | 7/2012 | Kumasaka | |
| 8,282,616 B2 | 10/2012 | Lehto et al. | |
| 8,361,913 B2 | 1/2013 | Siqueira | |
| 2002/0055727 A1 * | 5/2002 | Magnusson et al. | 604/358 |
| 2002/0092604 A1 | 7/2002 | McCabe et al. | |
| 2003/0000620 A1 | 1/2003 | Herrin et al. | |
| 2003/0060792 A1 * | 3/2003 | Harriz et al. | 604/385.04 |
| 2004/0064125 A1 | 4/2004 | Justmann et al. | |
| 2004/0102757 A1 | 5/2004 | Olson | |
| 2004/0111075 A1 * | 6/2004 | Loyd | 604/385.01 |
| 2006/0149208 A1 | 7/2006 | Carr | |
| 2006/0247591 A1 | 11/2006 | Hughes et al. | |
| 2007/0073262 A1 | 3/2007 | Babusik et al. | |
| 2007/0208318 A1 | 9/2007 | Loritz et al. | |
| 2008/0134487 A1 | 6/2008 | Harlono | |
| 2008/0287897 A1 | 11/2008 | Guzman Reyes et al. | |
| 2009/0157034 A1 | 6/2009 | Mattingly et al. | |
| 2010/0049155 A1 | 2/2010 | Soderbergh et al. | |
| 2010/0063468 A1 | 3/2010 | Lehto et al. | |
| 2010/0076390 A1 | 3/2010 | Norrby et al. | |
| 2011/0092941 A1 | 4/2011 | Ruman et al. | |
| 2011/0125122 A1 | 5/2011 | Thorson et al. | |
| 2011/0288518 A1 * | 11/2011 | Roe et al. | 604/385.14 |
| 2012/0241078 A1 | 9/2012 | Schlinz et al. | |
| 2012/0316523 A1 | 12/2012 | Hippe et al. | |

FOREIGN PATENT DOCUMENTS

| | | |
|---|---|---|
| EP | 0638304 | 3/1999 |
| EP | 0941727 | 9/1999 |
| EP | 0955976 | 3/2002 |
| EP | 2022453 A1 | 2/2009 |
| GB | 2250921 | 6/1992 |
| JP | 2007195792 | 8/2007 |
| WO | 9412135 A1 | 6/1994 |
| WO | 0037009 | 6/2000 |
| WO | 0188245 | 11/2001 |
| WO | 02053078 A1 | 7/2002 |
| WO | 2004047703 A1 | 6/2004 |

* cited by examiner

ABSORBENT ARTICLE HAVING AN ABSORBENT ASSEMBLY WITH INTEGRAL CONTAINMENT FLAPS

FIELD

The present invention relates generally to absorbent articles intended for personal wear and, more particularly, to an absorbent article having an absorbent assembly with integral containment flaps.

BACKGROUND

Absorbent articles such as diapers, training pants, incontinence garments, and the like conventionally include a liquid permeable body-facing liner, a liquid impermeable outer cover, and an absorbent core (also referred to as an absorbent body or absorbent structure) formed separate from the outer cover and liner. The absorbent core is disposed between the body-facing liner and the outer cover, and positioned at least within a crotch region of the article for receiving and retaining body exudates (e.g., urine, menses, blood) exuded by the wearer.

Some known absorbent articles include containment flaps attached to the body-facing liner to contain and/or inhibit body exudates exuded by the wearer from leaking out of the absorbent article. Such containment flaps are typically formed by folding a nonwoven material and bonding the folded material to the body-side liner. The containment flaps are typically spaced-apart and extend in a longitudinal direction of the absorbent article. The containment flaps are typically attached to the body-side liner laterally inward of the side edges of the body-side liner to provide an attachment region located laterally outwards of the containment flaps for attaching the body-side liner to the outer cover.

The outer covers of such absorbent articles typically include an attachment region corresponding to the attachment region of the body-side liner for bonding the body-side liner to the outer cover. The containment flaps, body-side liners, and outer covers requires additional material in the crotch region along lateral outer portions of the body-side liner and the outer cover for attaching the body-side liner to the outer cover outward from the containment flaps. Such additional material causes the crotch region to be wider than functionally necessary. Further, such additional material through the crotch region of the absorbent article typically has a "ruffled" appearance along the lateral outer portions. Such characteristics are often undesirable, particularly in absorbent articles designed to look like underwear, which typically have relatively narrow, unruffled crotch regions.

There is a need, therefore, for an absorbent article and methods of manufacturing such an absorbent article having containment flaps configured to decrease the overall width of the crotch region of the article, while maintaining the performance of the article and providing an underwear like look, fit and feel.

SUMMARY

In one aspect, a disposable absorbent assembly generally comprises a liquid permeable bodyside liner, a liquid impermeable backsheet, and an absorbent structure disposed between the liner and the backsheet; and. A pair of laterally opposed containment flaps is integrally formed from the bodyside liner. The backsheet extends into the containment flaps.

In another aspect, an absorbent assembly generally comprises a bodyside liner including a central zone having a first liquid permeability and lateral outer zones each having a second liquid permeability. The second liquid permeability of the lateral outer zones is less than the first liquid permeability of the central zone. The absorbent assembly also comprises a liquid impermeable backsheet and an absorbent structure disposed between the liner and the backsheet. A pair of laterally opposed containment flaps is integrally formed from the bodyside liner.

In yet another aspect, an absorbent assembly generally comprises a liquid permeable bodyside liner and an absorbent structure. A pair of laterally opposed containment flaps is integrally formed from the bodyside liner and formed by folding the bodyside liner over and adhering the bodyside liner to itself along two longitudinally extending adhesive seams. Each containment flap includes a fixed edge and a free edge opposite the fixed edge. Each of the adhesive seams is adjacent an inner side of the fixed edge of the respective containment flap.

Other features of the invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
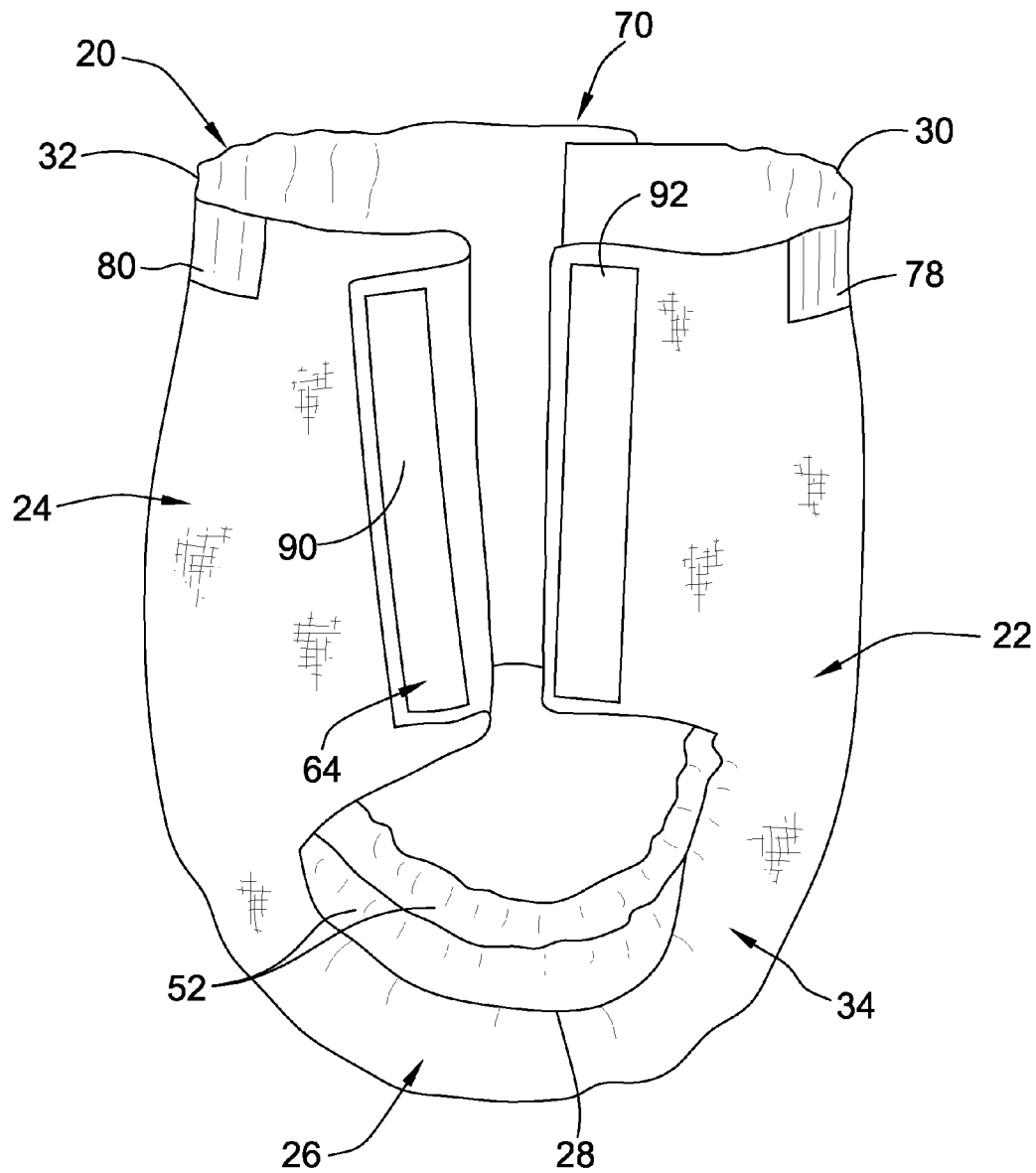
FIG. 1 is a side perspective of one suitable embodiment of an absorbent article shown in the form of a training pant, the training pant having a mechanical fastening system fastened on one side of the training pant and unfastened on the opposite side thereof.

Referring now to the drawings and in particular to FIG. 1, one suitable embodiment of an absorbent article is illustrated in the form of a child's toilet training pant and is indicated in its entirety by the reference numeral 20. The term absorbent article generally refers to articles that may be placed against or in proximity to a body of a wearer to absorb and/or retain various exudates from the body. The absorbent training pant 20 may or may not be disposable. Disposable refers to articles that are intended to be discarded after a limited period of use instead of being laundered or otherwise conditioned for reuse. It is understood that the embodiments of the present disclosure are suitable for use with various other absorbent articles intended for personal wear, including but not limited to diapers, swim diapers, feminine hygiene products (e.g., sanitary napkins), incontinence products, medical garments, surgical pads and bandages, other personal care or health care garments, and the like without departing from the scope of the present disclosure.

By way of illustration only, various materials and methods for constructing training pant such as the pant 20 of the various aspects of the present disclosure are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al., which are incorporated herein by reference.

Figure 2:
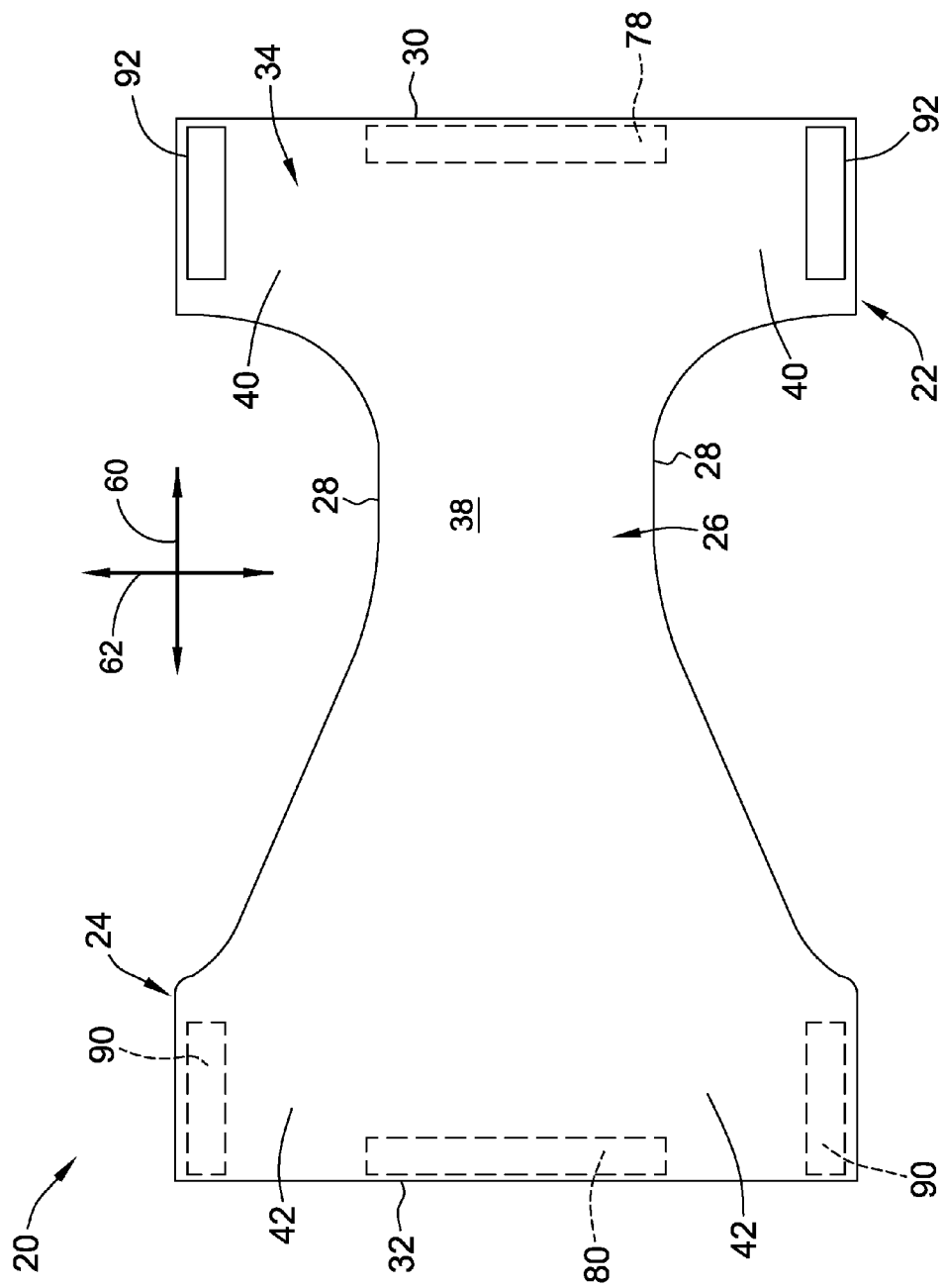
FIG. 2 illustrates a bottom plan view of the absorbent article of FIG. 1 with the training pant in an unfastened, unfolded and laid flat condition, and showing a surface of the training pants adapted to face away from the wearer during use.
Figure 3:
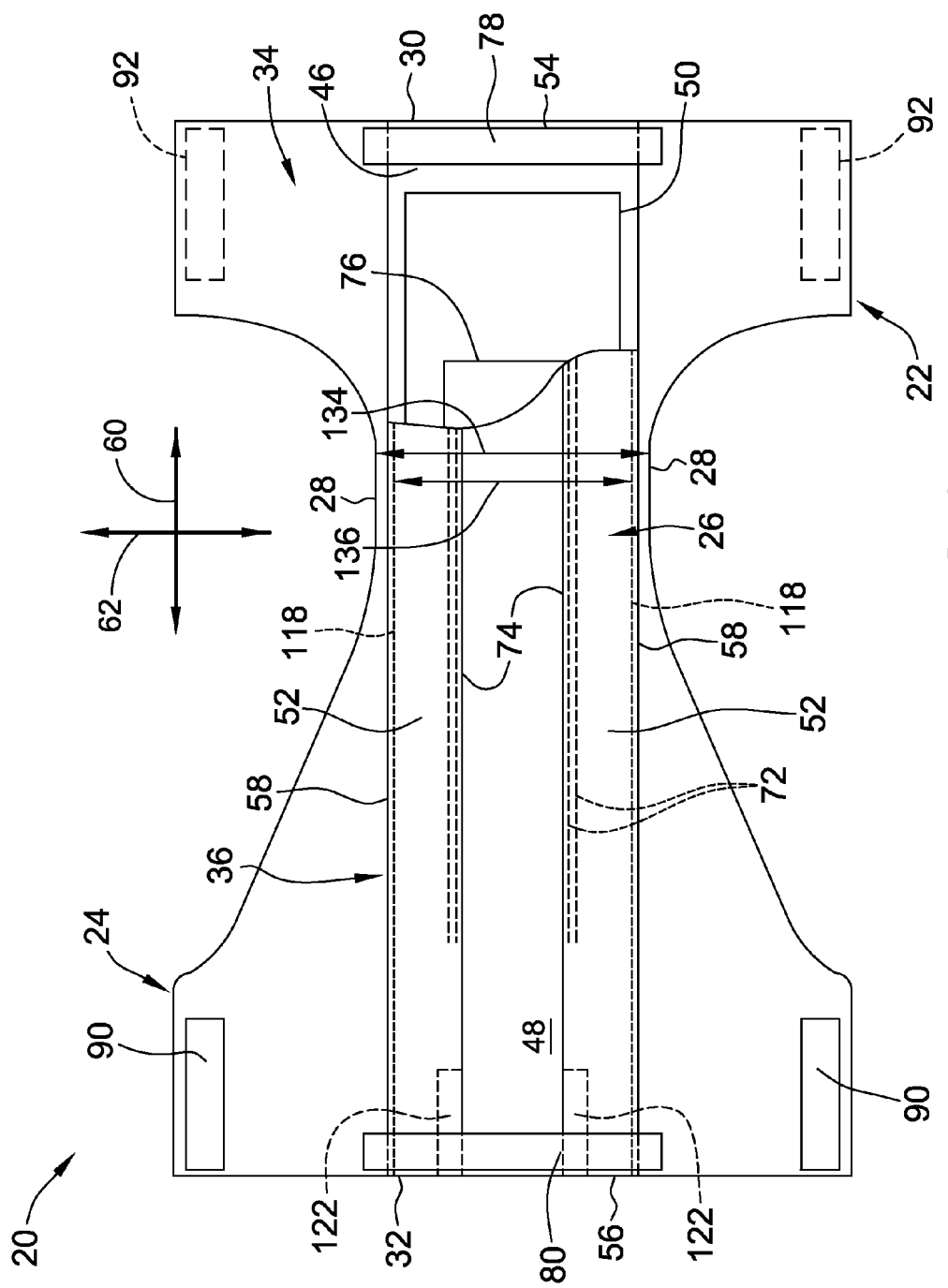
FIG. 3 illustrates a top plan view similar to FIG. 2 but showing a surface of the training pant adapted to face the wearer during use, portions of the training pant being cut away to show underlying features.

As seen in FIGS. 1-3, the training pant 20 has a front waist region 22, a back waist region 24, and a crotch region 26 disposed longitudinally between and interconnecting the front and back waist regions. The front waist region 22, the back waist region 24 and the crotch region 26 are indicated generally by the respective reference numbers. The training pant 20 also has a pair of laterally opposite side edges 28 and a pair of longitudinally opposite waist edges, respectively designated front waist edge 30 and back waist edge 32. The front waist region 22 is contiguous with the front waist edge 30, and the back waist region 24 is contiguous with the back waist edge 32.

With reference to FIGS. 2 and 3, the training pant 20 includes a chassis, indicated generally at 34, and an absorbent assembly, indicated generally at 36, attached to the chassis 34. Arrows 60 and 62 in FIGS. 2 and 3 depict the orientation of a longitudinal axis and a transverse or lateral axis, respectively, of the training pant 20. The illustrated absorbent assembly 36 extends longitudinally from the front waist region 22 through the crotch region 26 to the back waist region 24. While the illustrated absorbent assembly 36 is shown and described herein as extending from the crotch region 26 into both the front and back waist regions 22 and 24, it is contemplated that the absorbent assembly 36 may extend from the crotch region 26 into primarily the front waist region 22, or into primarily the back waist region 24, without departing from some aspects of this disclosure. Further, the absorbent assembly 36 may extend any suitable length along the crotch region 26 and/or into the front waist region 22 and/or the back waist region 24.

In the illustrated embodiment, the chassis 34 and the absorbent assembly 36 are formed separately from one another. It is contemplated, however, that the chassis 34 and the absorbent assembly 36 may be integrally formed with one another in some embodiments. It is further contemplated that in some suitable embodiments the absorbent assembly 36 can be disposable and the chassis 34 can be non-disposable. It is further contemplated that the absorbent assembly 36 can be configured to be inserted into conventional underwear. For example, the absorbent assembly 36 can include garment adhesive, as is known in the art, for adhering the absorbent assembly to the underwear. In such an embodiment, the underwear would define the chassis 34.

As seen in FIGS. 2 and 3, the chassis 34 includes a longitudinally extending central portion 38, a pair of laterally opposite front side portions 40 extending outward from the central portion 38 at the front waist region 22 (thereby forming transversely outer portions of the front waist region, and more broadly in part forming transversely opposite sides of the training pant), and a pair of laterally opposite back side portions 42 extending outward from the central portion at the back waist region 24 (thereby forming transversely outer portions of the back waist region, and together with the front side portions 40 further defining the sides of the pant). In the illustrated embodiment, the central portion 38 extends from the front waist region 22 through the crotch region 26 to the back waist region 24 of the training pant 20.

In one suitable embodiment and as seen in FIGS. 2 and 3, the front side portions 40, the back side portions 42, and the central portion 38 are formed from the same sheet of material. In other suitable embodiments, one or more of the front side portions 40, the back side portions 42, and/or the central portion 38 may be formed from two or more separate elements. For example, in one suitable embodiment, the front side portions 40 and/or the back side portions 42 can be formed separately from and attached to the central portion 38. It is contemplated that in some suitable embodiments, the back side portions, the front side portions, or the central portion 38 (at least in the crotch region 26 of the training pant 20) can be omitted. For example, in one such embodiment, the central portion 38 can be omitted from the region 26 of the training pant 20. The front side portions 40 and the back side portions 42 can then be formed from separate sheets of material (in which case the front side portions 40 and back side portions 42 are more accurately described as panels). For example, in the embodiment illustrated in FIG. 9, a training pant 420 includes front and back side panels 502, 504 formed separately from and secured to the absorbent assembly 36, described in more detail below. In such an embodiment, at least a portion of the crotch region 26 of the training pant 20 is free of the chassis.

The chassis 34 has a minimum width 134 taken along the lateral axis 62 of the training pant 20. In the illustrated embodiment of FIG. 3, the minimum width 134 is located along the central portion 38 of the chassis 34, and within the crotch region 26 of the training pant 20. The minimum width 134 of the illustrated chassis 34 generally corresponds to a portion of the training pant that is positioned between the legs of the wearer and covers the lower torso of the wearer, specifically the perineum region of the wearer.

The chassis 34 may comprise any suitable material including, for example and without limitation, a liquid permeable material that provides a generally cloth-like texture. The chassis 34 can be a single layer of material, or a multi-layered laminate structure. The chassis 34 or portions thereof may also be made of those materials of which the liquid permeable bodyside liner 48 is made. In other suitable embodiments, it is contemplated that the chassis 34 can be liquid impermeable. It is further contemplated that the chassis 34 can be vapor impermeable or vapor permeable (i.e., "breathable"). One suitable "breathable" material is composed of a microporous polymer film or a nonwoven fabric that has been coated or otherwise treated to impart a desired level of liquid impermeability.

It is also contemplated that the chassis 34 may be stretchable, and more suitably elastic. In particular, the chassis 34 is suitably stretchable and more suitably elastic in at least the transverse, or circumferential direction of the pant 20. In other embodiments, the chassis 34 may be stretchable, and more suitably elastic, in both the transverse and the longitudinal direction. It is contemplated that the chassis 34 can be stretchable in any suitable direction.

The absorbent training pant 20 and more specifically the chassis 34 may include a front waist elastic member 78, a rear waist elastic member 80, and/or leg elastic members (not shown), as are known to those skilled in the art. The waist elastic members 78, 80 can be attached to the inner surface of the chassis 34 (i.e., the surface of the chassis that faces the wearer when worn) or the outer surface of the chassis 34 (i.e., the surface of the chassis that faces away from the wearer). Likewise, the leg elastic members can be attached to the inner surface of the chassis 34 or the outer surface of the chassis 34 along the opposite side edges 28 and positioned in the crotch region 26 of the absorbent training pant 20. The leg elastic members can be longitudinally aligned along side edges 58 of the absorbent assembly 36, or, as shown in FIG. 3, the leg elastic members can be aligned with the opposite side edges 28 of the absorbent article.

While the training pant 20 of the illustrated embodiment has a pair of refastening seams 70 disposed on the side of the pant (one seam being illustrated in FIG. 1), it is understood that the seams can be located at any suitable location on the pant and that the seams can be permanently attached (e.g., by adhesive, thermal bonding, pressure bonding, thermal bonding). Moreover, while the illustrated refastening seams 70 are defined by a loop fastening components 90 (broadly, a "first fastening component") selectively engagement with hook fastening components 92 (broadly, a "second fastening component"), it is contemplated that any suitable refastenable fasteners can be used such as other types of mechanical fasteners, adhesive fasteners, cohesive fasteners.

Figure 4:
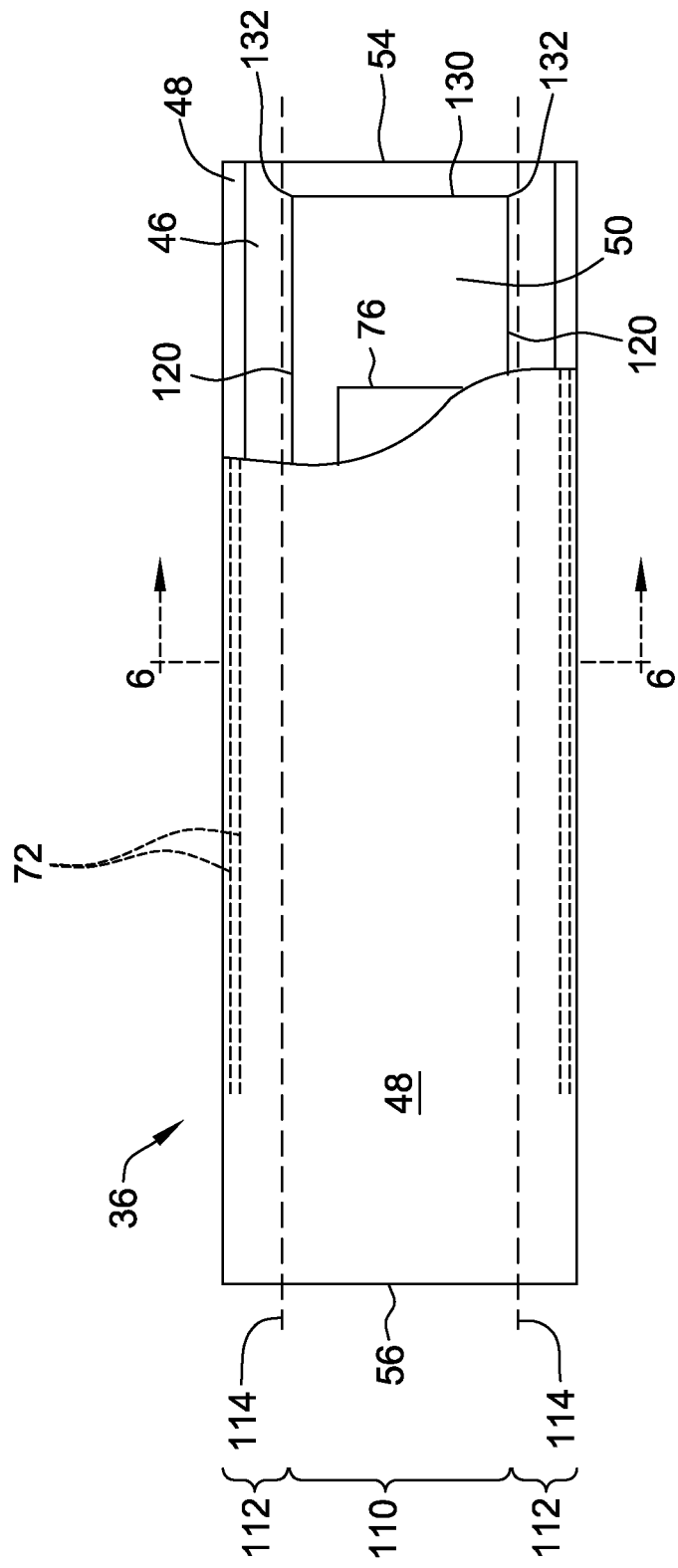
FIG. 4 is a top plan view of one suitable embodiment of an absorbent assembly suitable for use with the training pant of FIGS. 1-3 in an unfolded and laid flat configuration, portions of the absorbent assembly being cut away to show underlying features.

Referring to FIGS. 3 and 4, the absorbent assembly 36 of the illustrated embodiment is attached to the chassis 34 along at least the crotch region 26 of the absorbent training pant 20 by an adhesive, ultrasonic bonds, thermal bonds, pressure bonds, or the like. Suitable adhesives can be applied continuously or intermittently as beads, a spray, parallel swirls, or the like. Suitable ultrasonic bonds, pressure bonds, and/or thermal bonds can be formed continuously or intermittently along the absorbent assembly 36 to effect the attachment of the absorbent assembly 36 to the chassis 34. In the illustrated embodiment, the absorbent assembly 36 is permanently attached to the chassis 34. The term "permanently attached" is synonymous with terms such as "permanently joined," "permanently adhered," and "permanently bonded," and is intended herein to refer to an attachment that is generally not releasable without some damage or substantially reduced functionality of the components that are permanently attached. In another suitable embodiment, the absorbent assembly 36 is releasably attached to the chassis 34 by refastenable fasteners suitable for absorbent articles, such as adhesive fasteners, cohesive fasteners, mechanical fasteners (e.g., interlocking geometric shaped materials, such as hooks, loops, bulbs, mushrooms, arrowheads, balls on stems, male and female mating components, buckles, snaps) or the like.

While the absorbent assembly 36 illustrated in FIG. 3 is shown and described herein as being attached to the chassis 34 along the crotch region 26, it is contemplated that the absorbent assembly 36 may be attached to the chassis 34 along any one or more of the crotch region 26, the front waist region 22, and/or the back waist region 24, without departing from the scope of this disclosure. Further, the absorbent assembly 36 may be attached to the chassis 34 along any suitable length and/or area of the chassis 34.

As seen in FIGS. 3 and 4, the illustrated absorbent assembly 36 is generally rectangular in shape having a front end 54, a back end 56, and longitudinally extending side edges 58. The absorbent assembly 36 is illustrated in FIGS. 3 and 4 as having a rectangular shape, although it is contemplated that the absorbent assembly 36 may have other suitable shapes without departing from the scope of the present disclosure. In the illustrated embodiment, the front and back ends 54, 56 of the absorbent assembly 36 define respective portions of the front and back waist edges 30, 32 of the training pant 20. It is contemplated, however, that the front end 54 and/or back end 56 of the absorbent assembly 36 can be spaced inward from the front and back waist edges 30, 32 of the training pant 20. In such an embodiment, the front and back waist edges 30, 32 of the training pant 20 are defined solely by the chassis 34. As illustrated in FIG. 3, the side edges 58 of the absorbent assembly 36 can be spaced slightly inward from the side edges 28 of the absorbent training pant 20. In other embodiments (see, e.g., FIG. 9), the opposite side edges 58 of the absorbent assembly 36 can form portions of the side edges 28 of the absorbent training pant 20. It is further contemplated that the front end 54 and/or back end 56 of the absorbent assembly 36 can be folded over (in a direction away from the chassis 34) to create a pocket.

In one suitable embodiment, the absorbent assembly 36 comprises a liquid impermeable backsheet 46 and a bodyside liner 48 attached to the backsheet in a superposed relation by suitable means such as adhesives, ultrasonic bonds, pressure bonds, thermal bonds or other conventional techniques. An absorbent structure (or absorbent core) 50 is disposed between the backsheet 46 and the bodyside liner 48. A pair of containment flaps 52 is integrally formed from the absorbent assembly 36, as described in more detail below, for inhibiting the lateral flow of body exudates.

In one suitable embodiment, the backsheet comprises a material which is substantially liquid impermeable. The backsheet 46 can be a single layer of liquid impermeable material, or may comprise a multi-layered laminate structure in which at least one of the layers is liquid impermeable. Multiple layers of the backsheet 46 may be suitably joined together by an adhesive, ultrasonic bonds, pressure bonds, thermal bonds, or the like. Suitable adhesives can be applied continuously or intermittently as beads, a spray, parallel swirls, or the like.

The backsheet 46 can be both liquid and vapor impermeable, or, more suitably, it may be liquid impermeable and vapor permeable. The backsheet 46 can be manufactured from a thin plastic film, although other flexible liquid impermeable materials may also be used. The backsheet 46 prevents waste material from wetting articles, such as bed sheets and clothing, as well as the wearer and caregiver.

In one suitable embodiment, the liquid impermeable material can permit vapors to escape from the interior of the disposable absorbent article, while still preventing liquids from passing through the backsheet 46. One suitable "breathable" material is composed of a microporous polymer film or a nonwoven fabric that has been coated or otherwise treated to impart a desired level of liquid impermeability.

It is also contemplated that the backsheet 46 may comprise a liquid permeable material, or the backsheet 46 may be omitted from the absorbent assembly 36 altogether. In such embodiments, the chassis 34 suitably comprises a liquid impermeable material to provide a liquid barrier to body exudates. In one embodiment in which the backsheet 46 is omitted, the bodyside liner 48 is attached to the chassis 34 such that the absorbent structure 50 is disposed between the bodyside liner 48 and the inner surface of the chassis 34. In another suitable embodiment, both the absorbent structure 50 and the bodyside liner 48 are attached to the chassis 34.

It is also contemplated that the backsheet 46 may be stretchable, and more suitably elastic. In particular, the backsheet 46 is suitably stretchable and more suitably elastic in at least the transverse, or circumferential direction of the pant 20. In other embodiments the backsheet 46 may be stretchable, and more suitably elastic, in both the transverse and the longitudinal direction.

The bodyside liner 48 is suitably compliant, soft-feeling, and non-irritating to the wearer's skin. The bodyside liner 48 is also sufficiently liquid permeable to permit liquid body exudates to readily penetrate through its thickness to the absorbent structure 50. Further, the bodyside liner 48 can be less hydrophilic than the absorbent structure 50 to present a relatively dry surface to the wearer and permit liquid to readily penetrate through its thickness. The hydrophilic/hydrophobic properties can be varied across the length, width and/or depth of the bodyside liner 48 and absorbent structure 50 to achieve the desired rate of fluid intake and dryness.

A suitable bodyside liner 48 may be manufactured from a wide selection of web materials, such as porous foams, reticulated foams, apertured plastic films, woven and non-woven webs, or a combination of any such materials. For example, the bodyside liner 48 may comprise a meltblown web, a spunbonded web, or a bonded-carded-web composed of natural fibers, synthetic fibers or combinations thereof. The bodyside liner 48 may be composed of a substantially hydrophobic material, and the hydrophobic material may optionally be treated with a surfactant or otherwise processed to impart a desired level of wettability and hydrophilicity. The surfactant can be applied by any conventional means, such as spraying, printing, brush coating or the like. The surfactant can be applied to the entire bodyside liner 48 or can be selectively applied to particular sections of the bodyside liner, such as the medial section along the longitudinal center line.

In some embodiments, a central zone 126 (FIG. 7) of the bodyside liner 48 (e.g., the portion of the bodyside liner 48 that is coextensive with and/or attached to the absorbent structure 50) and/or the portions of the bodyside liner 48 from which the containment flaps 52 are formed (referred to as lateral outer zones 128 (FIG. 7) of the bodyside liner 48) may be treated or otherwise coated to impart a desired level of liquid permeability or impermeability in the respective zones 126, 128. In one embodiment, the lateral outer zones 128 of the body side liner 48 are treated or coated such that the lateral outer zones 128 are less liquid-permeable than the central zone 126. In such embodiments, the backsheet 46 may extend only partially into the containment flaps 52, or, in some embodiments, not at all, as the bodyside liner 48 is sufficiently liquid impermeable along the containment flaps 52 to provide a barrier to the transverse flow of body exudates.

In one particularly suitable embodiment, the lateral outer zones 128 have a hydrostatic head greater than the hydrostatic head of the central zone 126. More specifically, the ratio of the hydrostatic head of the lateral outer zones 128 to the hydrostatic head of the central zone 126 is at least about 2, and more suitably, at least about 5. In one suitable example, the lateral outer zone has a hydrostatic head greater than about 40 cm, and more suitable, greater than about 100 cm.

Hydrostatic head is a measure of the liquid barrier properties of a fabric. Hydrostatic head refers to the height of water (in centimeters) which the fabric will support before a predetermined amount of liquid passes through. A fabric with a higher hydrostatic head reading indicates it has a greater barrier to liquid penetration than a fabric with a lower hydrostatic head. Materials having a suitable hydrostatic head, as well as methods of making such materials, are described in U.S. Pat. No. 5,482,765 issued Jan. 9, 1996 to Bradley et al.; U.S. Pat. No. 5,492,751 issued Feb. 20, 1996 to Butt, Sr. et al.; and U.S. Pat. No. 6,822,136 issued Nov. 23, 2004 to Niemeyer et al., which are incorporated herein by reference.

In yet other embodiments, the bodyside liner 48 may have a gradient of permeability, with greater permeability toward the central zone 126 of the liner 48. More particularly, the bodyside liner 48 may have greater permeability closer to the crotch region 26 of the absorbent training pant 20, and less permeability toward the free edge 74 of the containment flaps 52. Desired levels of liquid-permeability in the bodyside liner 48 can be rendered by zone-treating or otherwise coating selective portions of the bodyside liner 48 with surfactants, using desired liquid-permeable materials, or inducing permeability through partial or selective dispersibility.

In other embodiments, the bodyside liner 48 may be formed from different, discrete materials to obtain a desired level of liquid permeability or impermeability in the respective zones 126, 128. For example, in the alternative embodiment of FIG. 8, the absorbent assembly 236 includes a bodyside liner 304 comprising a liquid permeable central liner 306 and two liquid impermeable outer liners 308, described in more detail below.

The bodyside liner 48 may also be stretchable, and more suitably it may be elastomeric. Suitable elastomeric materials for construction of the bodyside liner 48 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers. The bodyside liner 48 can also be made from extensible materials as are described in U.S. patent application Ser. No. 09/563,417 filed on May 3, 2000 by Roessler et al. or from biaxially stretchable materials as are described in U.S. patent application Ser. No. 09/698,512 filed on Oct. 27, 2000 by Vukos et al., both references which are hereby incorporated by reference.

The absorbent structure 50 is disposed between the backsheet 46 and the bodyside liner 48 and has longitudinally opposite ends 130 (FIG. 4) and laterally opposite side edges 120 that meet at respective corner regions 132 of the absorbent structure 50. As used herein, the corner regions 132 of the absorbent structure 50 refer generally to those regions at which the edge margin of the absorbent structure 50 transitions from a longitudinal end to an adjacent lateral side edge. For example, in the illustrated embodiment, the longitudinal ends 130 of the absorbent structure 50 intersect (e.g., at a right angle) the lateral side edges 120 such that the corner regions 132 of the absorbent structure 50 are generally a defined point. However, it is contemplated that the corner regions 132 may be rounded, e.g., where the absorbent structure 50 is curved to define a rounded transition from the longitudinal ends 130 to adjacent lateral side edges 120, and remain within the meaning of the term corner region as used herein as well as within the scope of this disclosure. As such, the absorbent structure 50 of the illustrated embodiment has four defined corner regions 132, two of which are laterally spaced from each other at the front waist region 22 of the pant 20 (FIG. 4) and the other two of which are laterally spaced from each other at the back waist region 24 of the pant.

Figure 5:
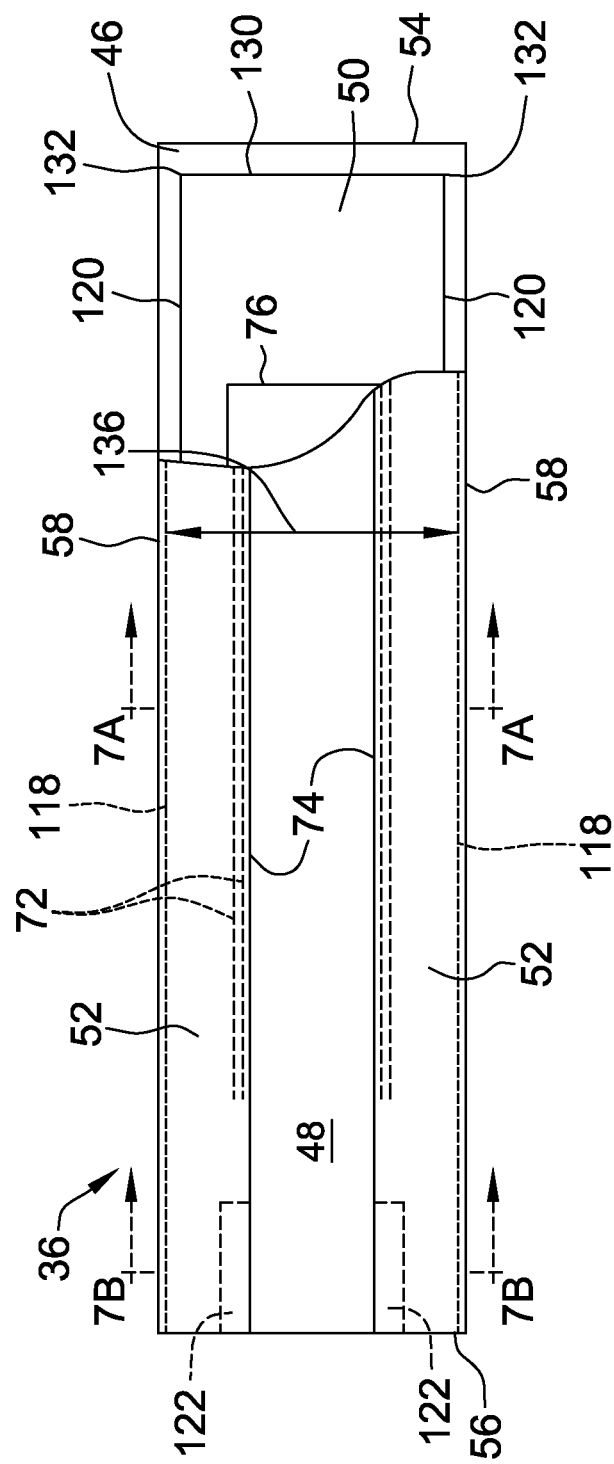
FIG. 5 is a top plan view of the absorbent assembly of FIG. 4 in a folded and laid flat configuration, portions of the absorbent assembly being cut away to show underlying features.

As seen in FIGS. 4 and 5, the illustrated absorbent structure 50 is generally rectangular. It is contemplated, however, that the absorbent structure 50 can have any suitable shape and size. For example, the absorbent structure 50 can include arcuate leg cutouts (e.g., by die cutting the absorbent structure) in the crotch region 26 of the training pant 20.

While the illustrated absorbent structure 50 is shown and described herein as extending from the crotch region 26 into both the front and back waist regions 22 and 24, it is contemplated that the absorbent structure may extend from the crotch region 26 into only the front waist region 22, or only the back waist region 24, without departing from the scope of this disclosure.

The absorbent structure 50 is suitably compressible, conformable, non-irritating to a wearer's skin, and capable of absorbing and retaining liquids and certain body wastes. For example, the absorbent structure 50 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent structure comprises a matrix of cellulosic fluff and superabsorbent hydrogel-forming particles. The cellulosic fluff may include a blend of wood pulp fluff. Suitable types of fluff include, for example, fluff pulp commercially available from Weyerhaeuser Company under the designation FR416 (7.5 percent Moisture) and CF416 (7.5 percent Moisture). Weyerhaeuser Company has offices in Federal Way, Wash., U.S.A.

The materials may be formed into a web structure by employing various conventional methods and techniques. For example, the absorbent structure 50 may be formed by a dry-forming technique, an air forming technique, a wet-forming technique, a foam-forming technique, or the like, as well as combinations thereof. Methods and apparatus for carrying out such techniques are well known in the art. Furthermore, the absorbent structure 50 may itself encompass multiple layers in a Z-direction (e.g., thickness) of the absorbent structure 50. Such multiple layers may take advantage of differences in absorbent capacity, such as by placing a lower absorbent capacity material layer closer to the liner 48 and a higher absorbent capacity material closer to the backsheet 46. Likewise, discrete portions of a single-layered absorbent structure may encompass higher capacity absorbents, and other discrete portions of the structure may encompass lower capacity absorbents.

Superabsorbent material is suitably present in the absorbent structure 50 in an amount of from about 0 to about 100 weight percent based on total weight of the absorbent structure 50. The absorbent structure 50 may suitably have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and preferably is capable of absorbing more than about 25 times its weight in liquid. Suitable superabsorbent materials are readily available from various suppliers. For example, Hysorb T 9700 superabsorbent, which is commercially available from BASF of Ludwigshafen, Germany, or Favor SXM 5600 superabsorbent, which is commercially available from Evonik of Essen, Germany.

The absorbent structure 50 may alternatively comprise a coform material. The term "coform material" generally refers to composite materials comprising a mixture or stabilized matrix of thermoplastic fibers and a second non-thermoplastic material. As an example, coform materials are made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the meltspun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference.

In one suitable embodiment, the absorbent structure 50 is stretchable so as not to inhibit the stretchability of other components to which the absorbent structure may be adhered, such as the backsheet 46 and bodyside liner 48. After being formed or cut to a desired shape, the absorbent structure 50 may be wrapped or encompassed by a suitable wrap (not shown) that aids in maintaining the integrity and shape of the absorbent structure.

The absorbent assembly 36 is configured to contain and/or absorb exudates discharged from the wearer. For example, the containment flaps 52 are configured to provide a barrier to the transverse flow of body exudates. A flap elastic member 72 (FIG. 3) may be operatively joined with each containment flap 52, as described in more detail below. The elasticized containment flaps 52 define a partially unattached, or free, edge 74 (FIG. 3) which assumes an upright configuration in at least the crotch region 26 of the absorbent training pant 20 to form a seal against the wearer's body during use. In one suitable embodiment, the containment flaps 52 can be located along the side edges 28 of the training pant 20, and can extend longitudinally along the entire length of the absorbent assembly 36 or may only extend partially along the length of the absorbent assembly 36.

In the illustrated embodiment, the absorbent assembly 36 also includes a surge management layer 76 located adjacent the absorbent structure 50 (e.g., between the absorbent structure 50 and the liner 48). The surge management layer 76 helps to decelerate and diffuse surges or gushes of liquid that may be rapidly introduced into the absorbent structure 50 of the training pant 20 by the wearer. Desirably, the surge management layer 76 can rapidly accept and temporarily hold the liquid prior to releasing the liquid into the storage or retention portions of the absorbent structure 50. Examples of suitable surge management layers are described in U.S. Pat. No. 5,486,166 issued Jan. 23, 1996 to Bishop et al.; U.S. Pat. No. 5,490,846 issued Feb. 13, 1996 to Ellis et al.; and U.S. Pat. No. 5,820,973 issued Oct. 13, 1998 to Dodge, II et al., the entire disclosures of which are hereby incorporated by reference herein.

Figure 6:
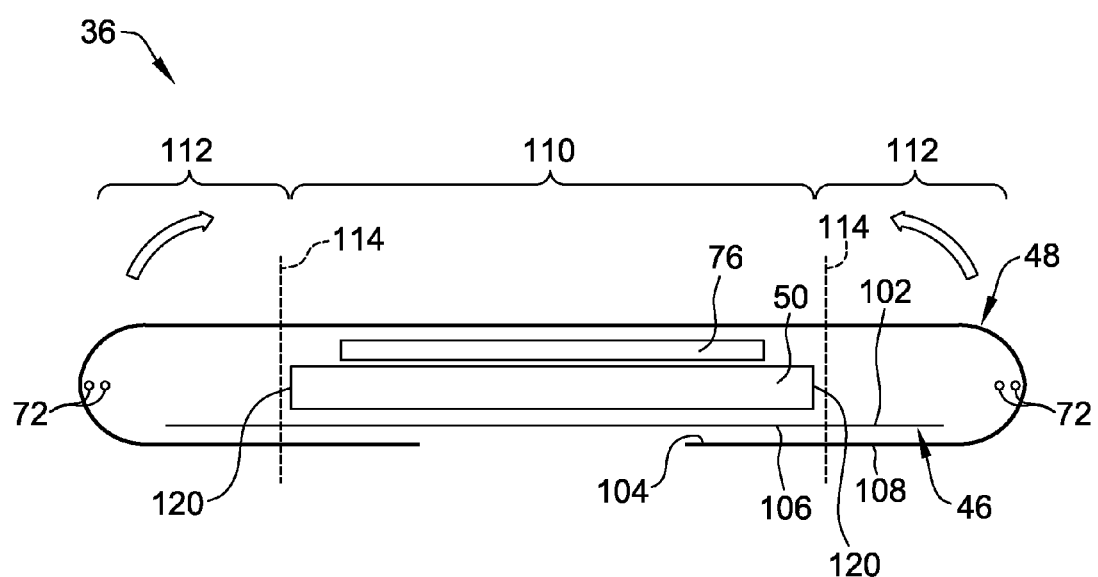
FIG. 6 is a cross-section of the absorbent assembly of FIG. 4 taken along line 6-6.

With particular reference now to FIGS. 3-7, the absorbent assembly 36 will be described in greater detail. FIG. 5 is a top plan view of the absorbent assembly 36 in an unfolded, laid flat configuration in which the containment flaps 52 have not been fully formed. Portions of the absorbent assembly 36 are cut away in FIG. 5 to show underlying features. FIG. 6 is a cross-section of the absorbent assembly 36 taken along line 6-6 of FIG. 5. The backsheet 46 and the bodyside liner 48 each include an inward-facing side 102, 104 (i.e., the side that faces the interior of the absorbent assembly 36), and an outward-facing side 106, 108 (i.e., the side that faces away from the interior of the absorbent assembly 36), respectively.

As shown in FIGS. 4-7, the bodyside liner 48 extends around the absorbent structure 50 and the backsheet 46 such that the inward-facing side 104 of the bodyside liner 48 overlaps the outward-facing side 106 of the backsheet 46. The absorbent structure 50 and the backsheet 46 are thereby enclosed within the bodyside liner 48. In the illustrated embodiment, the backsheet 46 is partially enclosed by the bodyside liner 48, although it is contemplated that the backsheet 46 may be fully enclosed by the bodyside liner. The bodyside liner 48 is attached to the backsheet 46 using suitable means such as adhesives, ultrasonic bonds, pressure bonds, thermal bonds or other conventional techniques. The bodyside liner 48 can be attached to the backsheet 46 along the inward-facing side 102 and/or the outward-facing side 106 of the backsheet 46. In one suitable embodiment, the bodyside liner 48 is attached to the backsheet 46 along the portion of the bodyside liner 48 that overlaps the outward-facing side 106 of the backsheet 46.

The absorbent structure 50 is disposed between the bodyside liner 48 and the backsheet 46 along a central region 110 of the absorbent assembly 36. In one suitable embodiment, the absorbent structure 50 is attached the bodyside liner 48 and/or the backsheet 46 using suitable means such as adhesives, ultrasonic bonds, pressure bonds, thermal bonds or other conventional techniques. In the illustrated embodiment, the absorbent structure 50 is attached to both the bodyside liner 48 and the backsheet 46. It is understood, however, that the absorbent structure 50 does not need to be bonded to either the bodyside liner 48 or the backsheet 46.

The absorbent assembly 36 illustrated in FIG. 5 also includes lateral outer regions 112 extending laterally outward from the central region 110 from which the containment flaps 52 are formed. Flap elastic members 72 are positioned within each lateral outer region 112 such that the flap elastic members 72 are positioned within the containment flaps 52 once formed. The containment flaps 52 are formed by folding the lateral outer portions 112 laterally inwards as indicated by the arrows in FIG. 6 about longitudinal fold lines 114, which is illustrated in FIG. 5, into face-to-face contact with the outward-facing side 108 of the bodyside liner 48 along the central region 110 of the absorbent assembly 36.

The lateral outer regions 112 are suitably attached to the bodyside liner 48 by an adhesive seam 116 extending longitudinally along the absorbent assembly 36, thereby forming a fixed edge 118 (FIGS. 3 and 7) of each containment flap 52. Suitable adhesives can be applied continuously or intermittently to the bodyside liner 48 as beads, a spray, parallel swirls, or the like. The adhesive seams 116 can extend any suitable length along the crotch region 26 of the pant 20. Further, it is contemplated that the adhesive seams 116 may extend into the front waist region 22 and/or the back waist region 24, and may even extend to the ends 54 and/or 56 of the absorbent assembly 36. In the illustrated embodiment, the adhesive seams 116 are aligned with laterally opposing side edges 120 of the absorbent structure 50.

A portion of the lateral outer regions 112 are left unattached to the bodyside liner 48, at least along a portion of the crotch region 26, to form the free edge 74 of the containment flaps 52. The free edge 74 of the containment flaps 52 is disposed opposite the fixed edge 118, and is configured to assume an upright configuration in at least the crotch region 26 of the absorbent training pant 20. More specifically, the flap elastic members 72 are positioned proximate the free edge 74 such that when a tensile force is applied to the flap elastic members 72, the free edges 74 of the containment flaps 52 assume an upright configuration to form a seal against the wearer's body during use.

The flap elastic members 72 may be formed from the same elastic materials as the waist elastic members 78, 80 and/or the leg elastic members, including sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate.

The flap elastic members 72 can extend any suitable length along the containment flaps 52. In the illustrated embodiment, the flap elastic members 72 extend less than the full length of the containment flaps 52. In one suitable embodiment, the flap elastic members 72 extend along the containment flaps 52 only within the crotch region 26 of the training pant 20. In another suitable embodiment, the flap elastic members 72 are generally coextensive with the absorbent structure 50. That is, in one embodiment, the flap elastic members 72 within the containment flaps 52 extend the length of the absorbent structure 50. It is understood, however, that the flap elastic members 72 can extend any suitable length along the containment flaps 52 including, for example, the full length of the containment flaps 52. In one suitable embodiment, for example, the flap elastic members 72 can extend into the flap attachment zones 122, described below with reference to FIG. 3.

The flap elastic members 72 can include active portions (i.e., portions of the flap elastic member 72 that are elastic) and inactive portions (i.e., portions of the flap elastic member 72 that are non-elastic). Portions of the flap elastic members 72 can be rendered inactive (i.e., non-elastic) by, for example, chopping or otherwise "deadening" the flap elastic members 72 along a desired inactive portion. The flap elastic members 72 can include any suitable number of active and inactive portions having any suitable dimension and configuration. In one suitable embodiment, for example, longitudinally opposing ends of the flap elastic members 72 can extend into the flap attachment zones 122 (FIG. 3), and can be rendered inactive within the flap attachment zones 122.

Figure 7A:
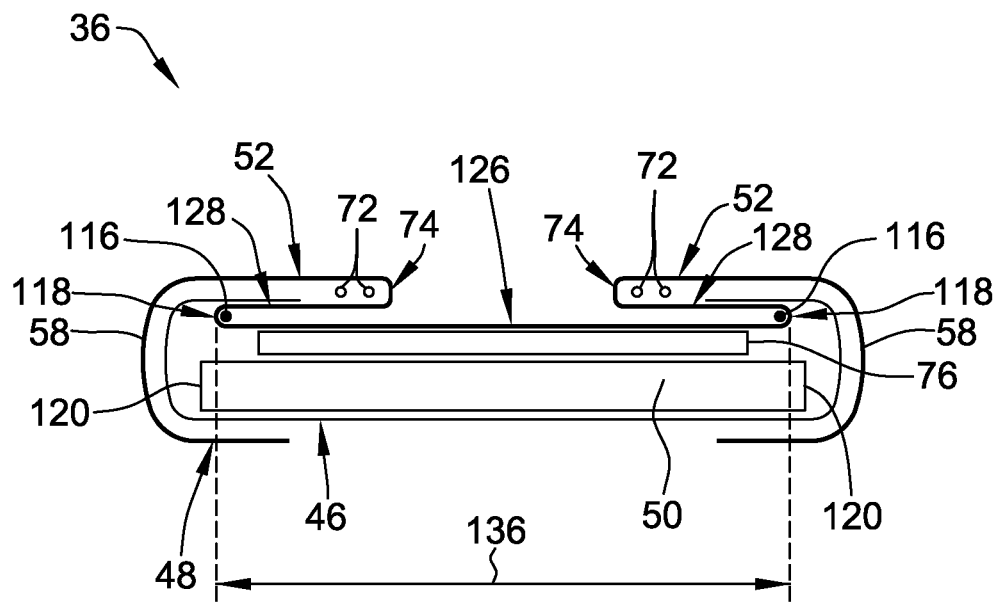
FIG. 7A is a cross-section of the absorbent assembly of FIG. 5 taken along line 7A-7A.
Figure 7B:
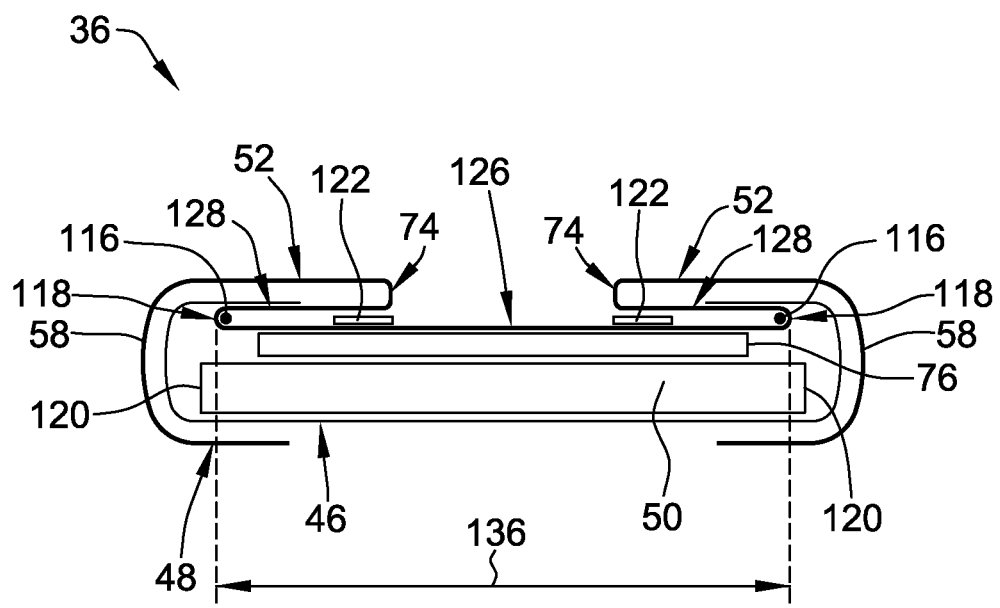
FIG. 7B is a cross-section of the absorbent assembly of FIG. 5 taken along line 7B-7B.

As shown in FIG. 7, when the containment flaps 52 are fully formed, the backsheet 46 is enclosed by the bodyside liner 48 within the containment flaps 52. More specifically, the containment flaps 52 comprise a portion of the backsheet 46 interposed between two layers of the bodyside liner 48. The backsheet 46 extends into the containment flaps 52 from the fixed edge 118 of a respective containment flap 52 towards the free edge 74 of the containment flaps. In the illustrated embodiment, the backsheet 46 suitably extends at least partially into the containment flaps 52 to provide a liquid impermeable layer within the containment flap 52. In the illustrated embodiment, the backsheet 46 extends only partially into the containment flap 52, although it is contemplated that the backsheet 46 may extend the entire length of the containment flap 52 to the free edge 74, or the backsheet 46 may not extend into the containment flap 52 at all.

The backsheet 46 can be suitably attached to the bodyside liner 48 and/or the absorbent structure 50 along the inward-facing side 102 and/or the outward-facing side 106 of the backsheet 46 by an adhesive, ultrasonic bonds, pressure bonds, thermal bonds, or the like. Suitable adhesives can be applied continuously or intermittently as beads, a spray, parallel swirls, or the like. In one suitable embodiment, the backsheet 46 is attached to the bodyside liner 48 within the containment flaps 52. More specifically, the outward-facing side 106 of the backsheet 46 is attached to the inward-facing side 104 of the bodyside liner 48 within the containment flaps 52. Alternatively, the inward-facing side 102 of the backsheet 46 is attached to the outward-facing side 108 of the bodyside liner 48 within the containment flaps 52.

In the illustrated embodiment, the backsheet 46 extends from within one containment flap 52, around the absorbent structure 50, and into the other containment flap 52, thereby forming a continuous liquid-impermeable barrier around the absorbent assembly 36. In some embodiments, it is contemplated that the backsheet 46 does not extend around the absorbent structure 50, and instead comprises segmented or discrete sheets of liquid impermeable material attached to the bodyside liner 48 within and/or proximate the containment flaps 52 such that the backsheet 46 forms a liquid impermeable barrier within the containment flaps 52. In such embodiments, the chassis 34 may suitably be formed of a liquid impermeable material to provide a liquid impermeable barrier between the absorbent structure 50 and the garment facing side of the pant 20.

As shown in FIGS. 3 and 7, the fixed edges 118 of the containment flaps 52 are separated by a lateral distance 136. In the illustrated embodiment, the containment flaps 52 and the fixed edges 118 of the containment flaps 52 are substantially parallel to one another. As a result, the lateral distance 136 between the fixed edges 118 is substantially the same along the length of the containment flaps 52. In the illustrated embodiment, the fixed edges 118 of the containment flaps 52 are offset from the side edges 58 of the absorbent assembly 36. In some embodiments, the fixed edges 118 of the containment flaps 52 may be formed proximate the side edges 58 of the absorbent assembly 36 such that the containment flaps 52 are disposed on and/or aligned with the side edges 58 of the absorbent assembly 36. In such embodiments, the difference between the lateral distance 136 and the overall width of the absorbent assembly 36 is substantially equal to the width of the containment flaps 52.

In addition to the adhesive seam 116, the containment flaps 52 may be attached to the bodyside liner 48 along end portions of the containment flaps 52. In the illustrated embodiment, the containment flaps 52 are attached to the bodyside liner 48 within the front waist region 22 and the back waist region 24 to define flap attachment zones 122 (FIGS. 3 and 5). For example, the flap attachment zones 122 may be formed within the front waist region 22 and/or the back waist region 24 to enable the waist edges 30, 32 to form a better seal around the wearer's waist. The flap attachment zones 122 suitably extend to the ends 54, 56 of the absorbent assembly 36, and may extend through the front waist region 22 and/or the back waist region 24 and into the crotch region 26 of the absorbent training pant 20. In another embodiment, the flap attachment zones 122 may extend from the ends 54, 56 of the absorbent assembly 36 and only partially through the front waist region 22 and/or the back waist region 24.

Figure 8A:
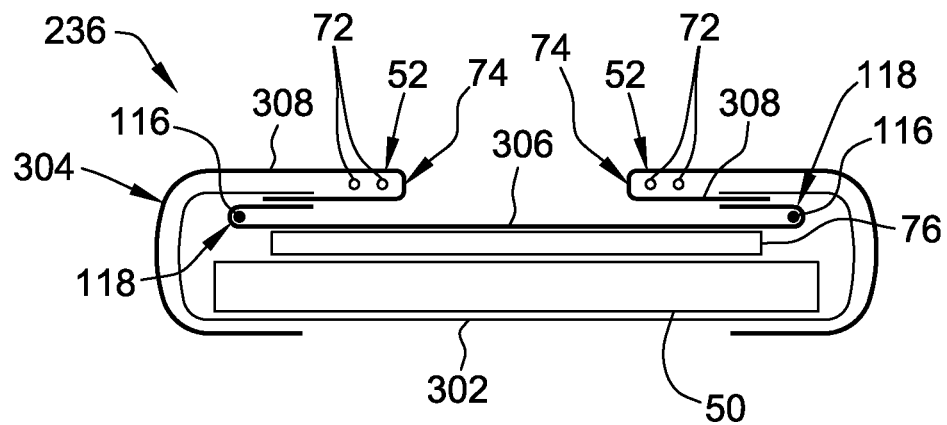
FIG. 8A is a cross-section of another suitable embodiment of an absorbent assembly for use with the training pant of FIGS. 1-3 taken through a crotch region of the absorbent assembly.
Figure 8B:
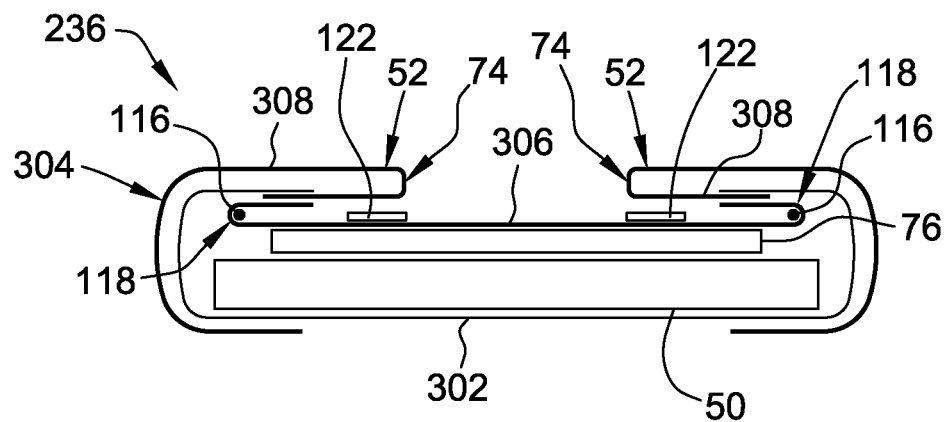
FIG. 8B is a cross-section of the embodiment of FIG. 8A taken through a back waist region of the absorbent assembly.

FIG. 8 illustrates another suitable embodiment of an absorbent assembly 236 suitable for use with the training pant 20 of FIGS. 1-3. The absorbent assembly 236 is substantially similar to the absorbent assembly 36 described above. More specifically, the absorbent assembly 236 is attached to a chassis (not shown in FIG. 8) and extends longitudinally from the front waist region 22 through the crotch region 26 to the back waist region 24 of the training pant 20. As with the absorbent assembly 36, it is contemplated that the absorbent assembly 236 may extend from the crotch region 26 into only the front waist region 22, or only the back waist region 24, without departing from the scope of this disclosure. Further, the absorbent assembly 236 may extend any suitable length along the crotch region 26 and/or into the front waist region 22 and/or the back waist region 24.

The illustrated absorbent assembly 236 is generally rectangular in shape having a front end, a back end and longitudinally extending side edges. While the absorbent assembly 236 is illustrated in FIG. 8 as having a rectangular shape, it is contemplated that the absorbent assembly 236 may have other suitable shapes without departing from the scope of the present disclosure.

In one suitable embodiment, the absorbent assembly 236 comprises a liquid impermeable backsheet 302 and a bodyside liner 304 attached to the backsheet 302 in a superposed relation by suitable means such as adhesives, ultrasonic bonds, pressure bonds, thermal bonds or other conventional techniques. An absorbent structure (or absorbent core) 50 is disposed between the backsheet 302 and the bodyside liner 304.

A pair of containment flaps 52 is integrally formed from the absorbent assembly 236 in the same manner as described above with reference to FIGS. 5-7. More specifically, lateral outer regions of the absorbent assembly 236 are suitably attached to the bodyside liner 304 by an adhesive seam 116 extending longitudinally along the absorbent assembly 236, thereby forming a fixed edge 118 of each containment flap 52.

As with the absorbent assembly 36, a portion of containment flaps 52 are left unattached to the bodyside liner 304, at least along a portion of the crotch region 26, to form free edges 74 of the containment flaps 52. The free edge 74 of the containment flaps 52 is disposed opposite the fixed edge 118, and is configured to assume an upright configuration in at least the crotch region 26 of the absorbent training pant 20. More specifically, flap elastic members 72 are positioned proximate the free edge 74 such that when a tensile force is applied to the flap elastic members 72, the free edges 74 of the containment flaps 52 assume an upright configuration to form a seal against the wearer's body during use.

The backsheet 302 may comprise the same materials and have the same configuration as the backsheet 46 described above with reference to FIGS. 3-7. In the embodiment illustrated in FIG. 8, the backsheet 302 may suitably comprise a liquid permeable material, or may suitably be omitted from the absorbent assembly 236 altogether as a result of the configuration of the bodyside liner 304.

The absorbent structure 50 may comprise the same materials and have the same configuration as the absorbent structure 50 described above with reference to FIGS. 3-7.

Similar to the absorbent assembly 36, the absorbent assembly 236 includes a surge management layer 76 located adjacent the absorbent structure 50 (e.g., between the absorbent structure 50 and the bodyside liner 304) to help decelerate and diffuse surges or gushes of liquid that may be rapidly introduced into the absorbent structure 50 of the training pant 20 by the wearer.

The absorbent assembly 236 differs from the absorbent assembly 36 in that the bodyside liner 304 of the absorbent assembly 236 comprises a liquid permeable central liner 306 and two liquid impermeable outer liners 308 attached to laterally opposing sides of the central liner 306. In the embodiment of FIG. 8, the containment flaps 52 are suitably formed from the liquid impermeable outer liners 308. The liquid permeable central liner 306 and the liquid impermeable outer liners 308 are suitably compliant, soft-feeling, and non-irritating to the wearer's skin. The central liner 306 is sufficiently liquid permeable to permit liquid body exudates to readily penetrate through its thickness to the absorbent structure 50.

The liquid impermeable outer liners 308 suitably comprise a material which is substantially liquid impermeable, yet is suitably compliant, soft-feeling, and non-irritating to the wearer's skin. One particularly suitable material for the outer liners 308 includes a spun-bonded/meltblown/spun-bonded (S/M/S) laminate. Other suitable materials for the outer liners 308, and methods of making such materials, are described in U.S. Pat. No. 5,492,751 issued Feb. 20, 1996 to Butt, Sr. et al., which is incorporated herein by reference.

Because the containment flaps 52 of the absorbent assembly 236 are formed from the liquid impermeable outer liners 308, the backsheet 302 does not need to extend into the containment flaps 52 to the same extent as embodiments in which the containment flaps 52 are formed from a liquid permeable bodyside liner. It is further contemplated that the backsheet 302 may be omitted from the absorbent assembly 236 altogether.

Figure 9:
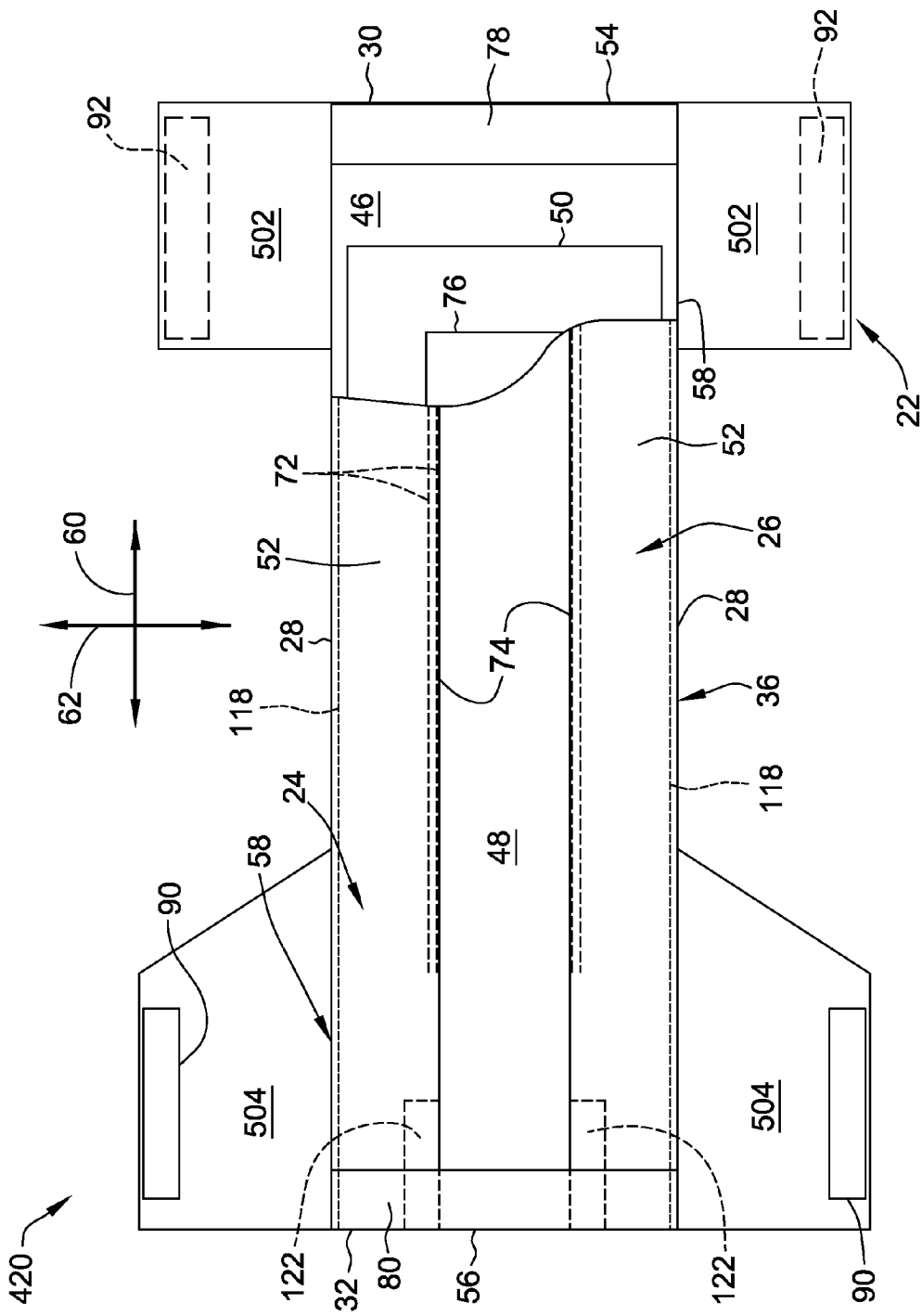
FIG. 9 is a top plan view of another suitable embodiment of an absorbent article in the form of a training pant showing a surface of the training pant adapted to face the wearer when worn, portions of the training pant being cut away to show underlying features.

FIG. 9 illustrates an alternative embodiment of an absorbent article, also in the form of a training pant 420, having discrete front and back side panels 502, 504 formed separately from and secured to the absorbent assembly 36. The side panels 502, 504 are permanently bonded to the absorbent assembly 36 in the respective front and back waist regions 22 and 24 of the pant 420. More particularly, the front side panels 502 can be permanently bonded to and extend transversely outward beyond the side edges 58 of the absorbent assembly 36 at the front waist region 22, and the back side panels 504 can be permanently bonded to and extend transversely outward beyond the side edges 58 of the absorbent assembly 36 at the back waist region 24. The side panels 502 and 504 may be bonded to the absorbent assembly 36 using attachment means known to those skilled in the art such as adhesive, thermal, pressure, or ultrasonic bonding.

The front and back side panels 502, 504, upon wearing of the pants 420, thus comprise the portions of the training pant 420 which are positioned on the hips of the wearer. The front and back side panels 502, 504 can be permanently bonded together to form the three-dimensional configuration of the pant 420, or be releasably connected with one another such as by the fastening system 64 of the illustrated aspects.

In the embodiment of FIG. 9, the side panels 502, 504 comprise an elastic material capable of stretching at least in a direction generally parallel to the lateral axis 62 of the training pant 420. Suitable elastic materials, as well as methods of incorporating elastic side portions into training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference.

Alternatively, the side panel material may include other woven or non-woven materials, such as those described herein as being suitable for construction of the chassis 34 and/or the bodyside liner 48, mechanically pre-strained composites, or stretchable but inelastic materials.

As a result of the containment flaps 52 being integrally formed with the absorbent assembly 36, no additional material is needed along the crotch region 26 of the training pant 20 to attach the containment flaps 52. As a result, the lateral width of the crotch region 26 of the absorbent training pant 20 may be smaller as compared to known training pant, thereby providing a more appealing look and feel. Further, because the containment flaps 52 are integrally formed from the absorbent assembly 36, a continuous liquid impermeable barrier is formed from the bodyside liner 48 and/or the polymer backsheet 46 that extends from the central region of the absorbent assembly out and around the lateral outer sides of the containment flaps 52. As a result, the barrier performance of the containment flaps 52 along the adhesive seams 116 is improved over known absorbent articles, which are generally susceptible to fluid leaks along the attachment seams of containment flaps.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A disposable absorbent assembly for use with an absorbent article having a front waist region, a back waist region, and a crotch region, the absorbent assembly comprising:
  a liquid permeable bodyside liner;
  a liquid impermeable backsheet;
  an absorbent structure disposed between the liner and the backsheet; and
  a pair of laterally opposed containment flaps integrally formed from the bodyside liner, the backsheet enclosed by the bodyside liner within the containment flaps, wherein the containment flaps are formed by folding the bodyside liner over and adhering the bodyside liner to itself along two longitudinally extending seams with adhesive at least in the crotch region of the absorbent article.

2. The disposable absorbent assembly set forth in claim 1 wherein the backsheet is attached to an inward-facing side of the bodyside liner within the containment flaps.

3. The disposable absorbent assembly set forth in claim 1 wherein the backsheet extends towards a free edge of the containment flaps.

4. The disposable absorbent assembly set forth in claim 3 wherein the backsheet extends to about the free edge of each containment flap.

5. The disposable absorbent assembly set forth in claim 1 wherein the bodyside liner includes a liquid permeable central zone and liquid impermeable lateral outer zones, the containment flaps being formed from the liquid impermeable lateral outer zones.

6. The disposable absorbent assembly set forth in claim 1 wherein each containment flap includes at least one elastic member.

7. The disposable absorbent assembly set forth in claim 1 wherein each containment flap includes a fixed edge and a free edge opposite the fixed edge, the free edge of each containment flap being attached to the bodyside liner within at least one of the front waist region and the back waist region to define a flap attachment zone.

8. The disposable absorbent assembly set forth in claim 1 wherein the bodyside liner extends around at least a portion of the backsheet and the absorbent structure.

9. An absorbent article comprising:
a chassis; and
the disposable absorbent assembly set forth in claim 1 attached to the chassis.

10. An absorbent assembly for use with an absorbent article having a front waist region, a back waist region, and a crotch region, the absorbent assembly comprising:
a bodyside liner including a central zone having a first liquid permeability and lateral outer zones each having a second liquid permeability, the second liquid permeability of the lateral outer zones being less than the first liquid permeability of the central zone;
a liquid impermeable backsheet;
an absorbent structure disposed between the liner and the backsheet; and
a pair of laterally opposed containment flaps integrally formed from the bodyside liner, wherein the containment flaps are adhered to itself along two longitudinally extending seams with adhesive at least in the crotch region of the absorbent article, each of the longitudinally extending seams overlying the absorbent structure.

11. The absorbent assembly set forth in claim 10 wherein the containment flaps are formed from the lateral outer zones of the bodyside liner.

12. The absorbent assembly set forth in claim 10 wherein the containment flaps are formed separately from and attached to the portion of the bodyside liner defining the central zone.

13. The absorbent assembly set forth in claim 10 wherein the lateral outer zones are liquid impermeable.

14. The absorbent assembly set forth in claim 10 wherein the lateral outer zones have a first hydrostatic head, and the central zone has a second hydrostatic head greater than the first hydrostatic head.

15. The absorbent assembly set forth in claim 14 wherein the ratio of the first hydrostatic head to the second hydrostatic head is at least about 2.

16. The absorbent assembly set forth in claim 10 wherein the central zone comprises a liquid permeable central liner, and the lateral outer zones comprise liquid impermeable outer liners, wherein the liquid impermeable outer liners are attached to laterally opposing sides of the central liner.

17. The absorbent assembly set forth in claim 16 wherein the containment flaps are formed from the outer liners.

18. The absorbent assembly set forth in claim 17 wherein the containment flaps are formed by folding the outer liners over and adhering the respective outer liner to itself.

19. An absorbent assembly comprising a liquid permeable bodyside liner and an absorbent structure, a pair of laterally opposed containment flaps being integrally formed from the bodyside liner and formed by folding the bodyside liner over about a foldline and adhering the bodyside liner to itself along two longitudinally extending adhesive seams, each of the longitudinally extending seams overlying the absorbent structure, each containment flap including a fixed edge and a free edge opposite the fixed edge, each of the adhesive seams being adjacent the foldline and disposed on an inner side of the fixed edge of the respective containment flap, each free edge of the containment flap being attached to the bodyside liner within a pair of flap attachment zones, each of the flap attachment zones of the respective pair of flap attachment zones being spaced apart and the respective adhesive seam extending longitudinally between the spaced apart attachment zones.

20. The absorbent assembly set forth in claim 19 further comprising a liquid impermeable backsheet wherein the backsheet extends into the containment flaps.

21. An absorbent article comprising:
a chassis; and
an absorbent assembly set forth in claim 19 attached to the chassis.

22. The absorbent article as set forth in claim 21 wherein the chassis is liquid impermeable.

23. The absorbent article as set forth in claim 21 wherein the chassis is liquid permeable.

24. The absorbent article as set forth in claim 21 wherein the bodyside liner extends around at least a portion of the absorbent structure.

25. The absorbent article as set forth in claim 19 wherein each of the adhesive seams extends the entire distance between the respective spaced apart attachment zones.

* * * * *